(12) United States Patent
Becq et al.

(10) Patent No.: US 8,252,958 B2
(45) Date of Patent: Aug. 28, 2012

(54) USE OF GUANABENZ AND ITS DERIVATIVES FOR MAKING DRUGS FOR TREATING CYSTIC FIBROSIS AND DISEASES RELATED TO A PROTEIN ADDRESSING DEFICIENCY IN THE CELLS

(75) Inventors: Frederic Becq, Poitiers (FR); Deborah Triboullard, Roscoff (FR); Marc Blondel, Saint-Pol de Leon (FR)

(73) Assignees: Centre National de la Recherche Scientifique (CNRS), Paris Cedex 16 (FR); Universite de Poitiers, Poitiers Cedex (FR)

( * ) Notice: Subject to any disclaimer, the term of this patent is extended or adjusted under 35 U.S.C. 154(b) by 569 days.

(21) Appl. No.: 12/085,588

(22) PCT Filed: Nov. 28, 2006

(86) PCT No.: PCT/FR2006/002600
§ 371 (c)(1),
(2), (4) Date: Apr. 1, 2009

(87) PCT Pub. No.: WO2007/060342
PCT Pub. Date: May 31, 2007

(65) Prior Publication Data
US 2009/0306430 A1 Dec. 10, 2009

(51) Int. Cl.
*C07C 241/00* (2006.01)
*C07C 243/00* (2006.01)
*A01N 37/52* (2006.01)
*A01N 33/02* (2006.01)
*A61K 31/155* (2006.01)
*A61K 31/135* (2006.01)

(52) U.S. Cl. ........ 564/251; 514/631; 514/634; 514/637; 514/646; 514/851

(58) Field of Classification Search .................. None
See application file for complete search history.

(56) References Cited

U.S. PATENT DOCUMENTS

| 5,665,739 A * | 9/1997 | Lang et al. .......... 514/345 |
| 6,412,962 B1 | 7/2002 | Kaspar |
| 6,413,962 B1 | 7/2002 | Naftchi |
| 2010/0036166 A1 * | 2/2010 | Bertolotti et al. ......... 564/228 |

FOREIGN PATENT DOCUMENTS

DE 18 02 394 5/1969

OTHER PUBLICATIONS

International Preliminary Report on Patentability and corrected version of English translation of Written Opinion dated Oct. 14, 2008, issued in connection with corresponding PCT/FR2006/002600.
International Search Report for PCT/FR2006/002600 mailed Mar. 5, 2008.
Becq F. et al.: "Pharmacological interventions for the correction of ion transport defect in cystic fibrosis" Expert Opinion on Therapeutic Patents 2004 United Kingdom, vol. 14, No. 10, pp. 1465-1483, XP002330339.
International Preliminary Report on Patentability and English translation of Written Opinion dated Jul. 8, 2008, issued in connection with corresponding PCT/FR2006/002600.

* cited by examiner

*Primary Examiner* — Susanna Moore
*Assistant Examiner* — Clinton Brooks
(74) *Attorney, Agent, or Firm* — Nixon & Vanderhye P.C.

(57) ABSTRACT

The invention concerns the use of guanabenz and its derivatives for making drugs for treating cystic fibrosis and diseases related to a protein addressing deficiency in the cells, said derivatives corresponding to formula (I), wherein: R=H or Cl and the phenyl group comprises two substituents, or a pharmaceutically acceptable salt of said derivatives.

8 Claims, 2 Drawing Sheets

Figure 1:
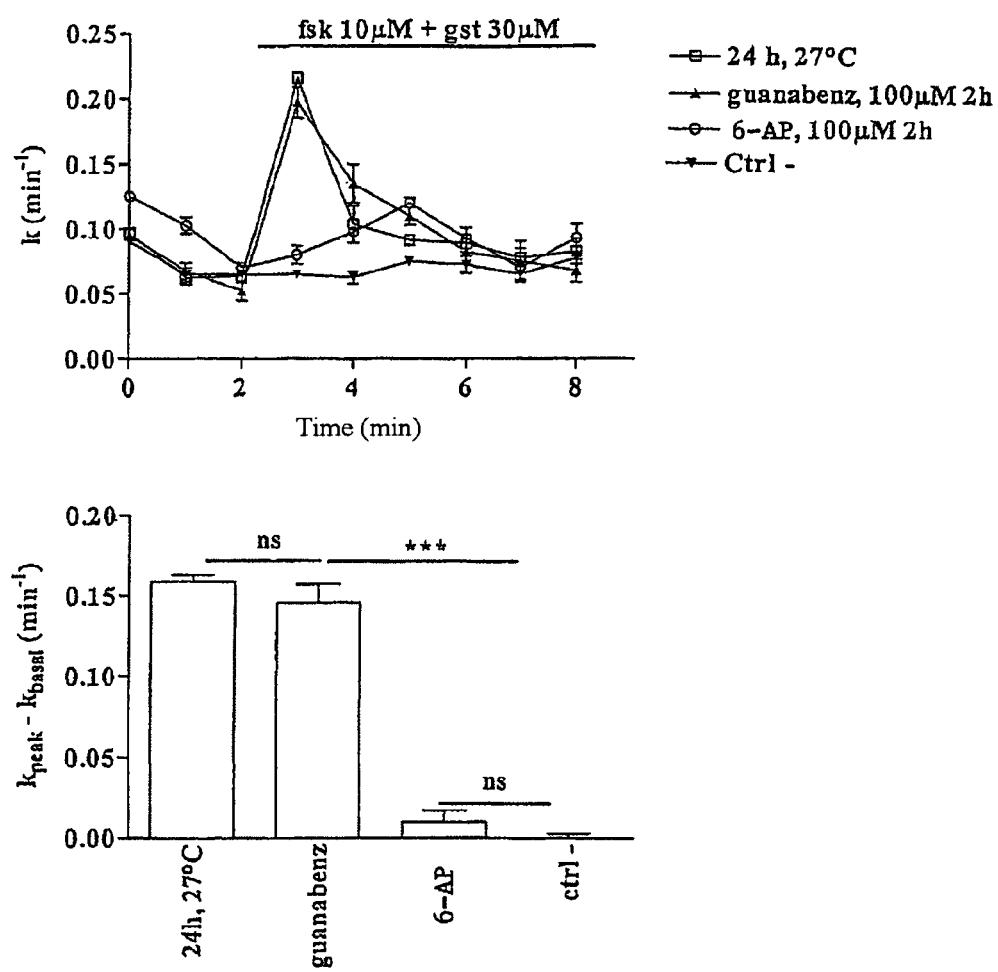

USE OF GUANABENZ AND ITS DERIVATIVES FOR MAKING DRUGS FOR TREATING CYSTIC FIBROSIS AND DISEASES RELATED TO A PROTEIN ADDRESSING DEFICIENCY IN THE CELLS

This application is the U.S. national phase of International Application No. PCT/FR2006/002600 filed 28 Nov. 2006 which designated the U.S. and claims priority to French Application No. 05/12023 filed 28 Nov. 2005, the entire contents of each of which are hereby incorporated by reference.

The invention relates to the use of guanabenz and of guanabenz derivatives for the manufacture of medicaments capable of restoring the addressing of endoplasmic reticulum proteins to plasma membranes.

A large number of human pathological situations exist in which an addressing deficiency is responsible for an adverse alteration of the location of proteins, and therefore of membrane composition and cell function. These diseases comprise cystic fibrosis, hyper-insulinemic hypoglycemia of infancy, neurodegenerative pathological conditions such as Parkinson's disease, hereditary emphysema, congenital long QT syndrome.

Readdressing of the proteins involved therefore constitutes a therapeutic means for these pathological conditions.

The functional organization of the eukaryotic cell is based on an elaborate system of membrane compartments or organelles (nucleus, endoplasmic reticulum, Golgi apparatus, endosomes) having their own protein and lipid composition. The addressing of proteins in the cell constitutes a set of molecular mechanisms which make it possible to bring about, during protein synthesis, good folding, processing and localization of functional proteins.

Cystic fibrosis (CF) is the most widespread lethal autosomal recessive genetic disease in European and North American populations. The CF gene (7q31 locus) encodes the trans-membrane protein termed CFTR (Cystic Fibrosis Transmembrane Conductance Regulator). This protein is a chloride channel located in the apical plasma membrane of pulmonary and digestive epithelial cells in healthy individuals.

Although there are over 1000 mutations of the CFTR protein, the most frequent mutation (70% of patients) is the deletion of a phenylalanine in the NBF1 domain at position 508 (delF508).

In CF patients, this protein is absent from plasma membranes because of a defective addressing of the protein which is retained in the endoplasmic reticulum (ER), and then degraded by the ubiquitin/proteasome system. In these patients, the cells whose CFTR protein is mutated in delF508 are no longer functional. Physiologically, CFTR is responsible for the trans-epithelial transport of water and electrolytes, and allows, in a healthy individual, the hydration of the pulmonary airways, good digestive secretory function and good exocrine gland function in general. One of the keys for the treatment of this disease, and in general of any pathological condition linked to such addressing problems, consists in a readdressing of the CFTR delF508 protein to the apical membrane of the cells. Once at the membrane, the CFTR delF508 transport activity may be stimulated by physiological agonists.

Surprisingly, the inventors have demonstrated that guanabenz, which has been clinically used for a long time for the treatment of hypertension, was capable of activating the wild-type CFTR and mutated forms and of causing a membrane relocation of the delF508-CFTR protein, thus restoring its transmembrane transport capacity.

This property has also been demonstrated with guanabenz derivatives. In general, these compounds are capable of restoring a protein addressing deficiency in cells.

Furthermore, they have the benefit of a high safety.

The aim of the invention is therefore to provide a novel use of these derivatives for the manufacture of medicaments for the treatment of cystic fibrosis and of diseases linked to a protein addressing deficiency in cells, in particular as indicated above.

The derivatives used in accordance with the invention correspond to the formula (I):

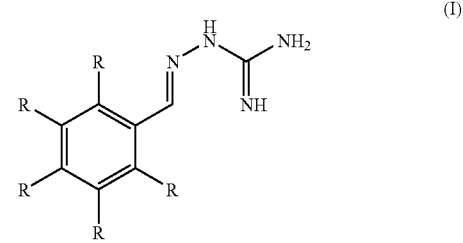

in which R=H or Cl and the phenyl group contains at least two substituents, or a pharmaceutically acceptable salt of these derivatives.

These derivatives are capable of restoring the addressing of the CFTR protein to the plasma membranes of cells and therefore constitute compounds of great interest for the treatment of pathological conditions related to such addressing deficiency problems. Among the diseases involved, there may be mentioned, in addition to cystic fibrosis, hyperinsulinemic hypoglycemia of infancy, neurodegenerative pathological conditions such as Parkinson's disease, hereditary emphysema, congenital long QT syndrome.

As illustrated by the examples, they are particularly effective for causing the relocation of the delF508-CFTR protein in cystic fibrosis where this protein is retained in the endoplasmic reticulum, and thus restoring its trans-membrane transfer capacity.

The invention relates in particular to the use of guanabenz and its salts.

The term "guanabenz", as used in the description and the claims, corresponds to the compound of formula (II):

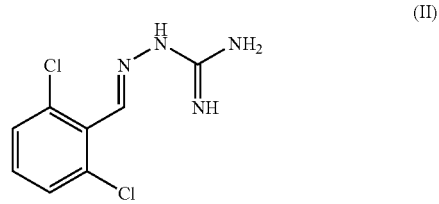

or to one of its salts, in particular the acetate of formula (III):

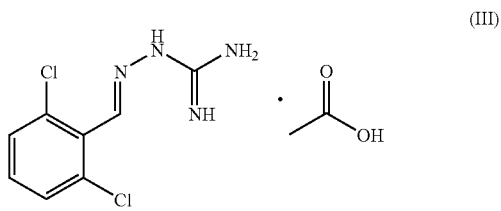

In another embodiment of the invention, the molecule used corresponds to the formula (IV):

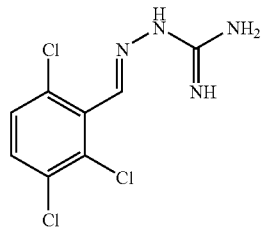

(IV)

or to a pharmaceutically acceptable salt.

During the manufacture of medicaments, the active ingredients, which are used in therapeutically effective quantities, are mixed with the pharmaceutically acceptable vehicles for the chosen mode of administration. These vehicles may be solids or liquids.

Accordingly, for oral administration, the medicaments are prepared in the form of gelatin capsules, tablets, sugar-coated tablets, capsules, pills, drops, syrups and the like. Such medicaments may contain from 1 to 100 mg of active ingredient per unit.

For administration by injection (intravenous, subcutaneous, intramuscular), the medicaments are provided in the form of sterile or sterilizable solutions.

They may also be in the form of emulsions or suspensions.

The medicaments of the invention are more particularly administered in the form of aerosols.

The doses per dosage unit may vary from 1 to 50 mg of active ingredient. The daily dosage is chosen so as to obtain a final concentration of at most 100 μM of guanabenz in the blood of the patient treated.

Other characteristics and advantages of the invention are given in the results presented below so as to illustrate the invention.

Figure 2:
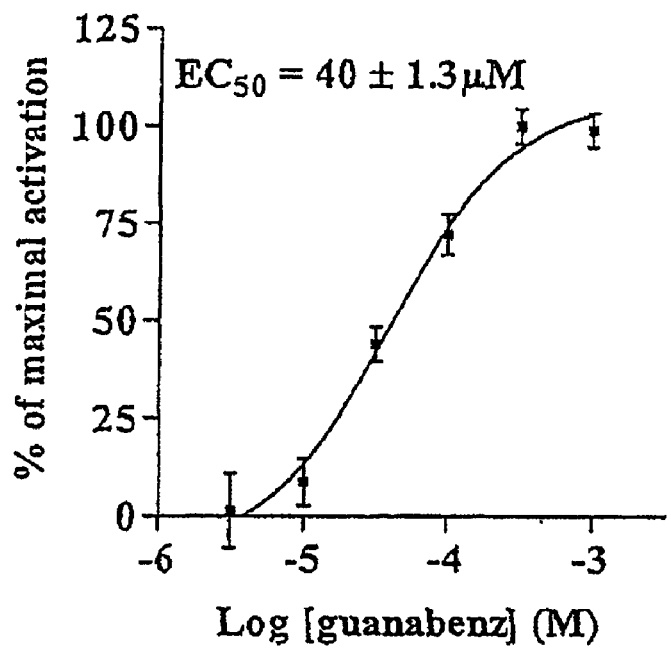
Figure 2:
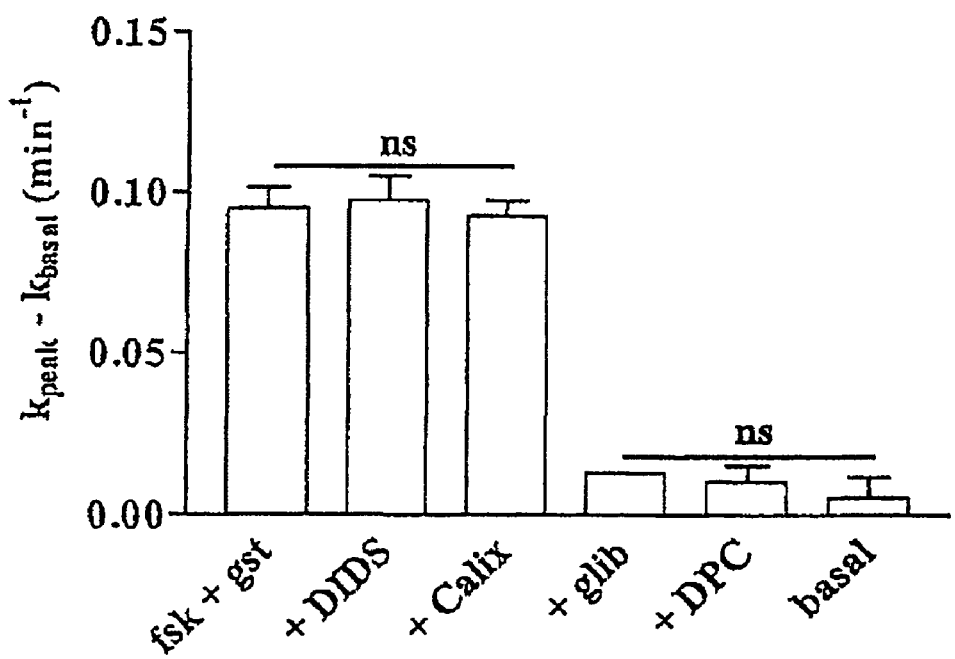

Reference is made therein to FIGS. 1 and 2, which represent, respectively:

FIGS. 1A and 1B: the activation of delF508-CFTR in CF15 cells after treatment with guanabenz;

FIG. 2A: the dose-response relationship observed with a 2 h treatment with guanabenz; and FIG. 2B: the pharmacological profile of the CFTR channels in CF15 cells after 2 h of incubation with guanabenz.

MATERIALS AND METHODS

M1. Cell Culture

CHO-WT cells: The CHO (Chinese hamster ovary) cells are fibroblasts which have been transfected with the wild-type CFTR(CFTR-WT) gene. These cells will therefore overexpress the CFTR protein.

Culture medium: MEM alpha medium (GIBCO)+7% of fetal calf serum+0.5% of penicillin/streptomycin+100 μM of methotrexate (amethopterin, Sigma).

CF15 cells: The CF15 cells are human epithelial cells of nasal origin which express the ΔF508-CFTR gene.

Culture medium: DMEM medium+HAM F12+10% of FCS+0.6% of penicillin/streptomycin+growth factors (insulin 5 μg/ml, transferrin 5 μg/ml, epinephrine 5.5 μM, adenine 0.18 mM, EGF 10 ng/ml, T3 2 nM, hydrocortisone 1.1 μM).

Calu-3 cells: The Calu-3 cells are human epithelial cells of pulmonary origin which express the wild-type CFTR gene.

Culture medium: DMEM/F12 medium with glutamax+7% of fetal calf serum+1% of penicillin/streptomycin.

M2. Immunolabeling

Immunolabeling makes it possible to visualize the cellular location of the CFTR protein using an anti-CFTR primary antibody (Ab), and then an anti-primary antibody secondary antibody labeled with the fluorophore Cy3.

The cells are inoculated beforehand on glass coverslips in the appropriate culture medium. Three washes with TBS (NaCl: 157 mM, Tris base: 20 μM, pH 7.4) of 5 min each are carried out. The cells are then fixed by adding TBS-paraformaldehyde (3%) for 20 min. After 3 washes with TBS (5 min), the cells are incubated with TBS-triton 0.1% (10 min) which allows the formation of holes in the cell membrane, and then 3 washes with TBS are again carried out before bringing the cells into contact with TBS-BSA 0.5%-saponin 0.05% for 1 h. The cells are then incubated with the anti-C terminal CFTR primary antibody (2 μg/ml) for 1 h. Three washes with TBS-BSA-saponin of 5 min each are carried out before the incubation with the secondary antibody GAM-cy3 (1/400) for 1 h. After 2 washes with TBS of 5 min, the nuclei are labeled by incubation with Topro3 (1/1000) for 5 min. Finally, the glass coverslips may be mounted on a slide after 3 final washes with TBS of 5 min. The slides are examined under a confocal microscope (Bio-Rad) using a laser excitation at the appropriate wavelengths. In order to differentiate the labeling between Cy3 and Topro3, the Topro3 fluorescence color was changed to blue (color of the nuclei).

M3. Efflux of Radiotracers

The measurements of chloride ion transport in the cells were performed with the aid of the radioactive iodide efflux technique (Becq et al., 1999; Dormer et al., 2001). The tracer ($^{125}$I) is incorporated into the intracellular medium. Next, the quantity of radiotracer which leaves the cell is counted after the addition of various pharmacological agents. The iodide is used as chloride ion transport tracer. $^{125}$I further has the advantage of having a short life compared with that of other markers such as $^{35}$Cl (respective ½ life: 30 days and 300 000 years).

The cells are cultured on 24-well plates in a suitable medium. Two rinses with efflux medium (NaCl: 136.6 mM, KCl: 5.4 mM, $KH_2PO_4$: 0.3 mM, $NaH_2PO_4$: 0.3 mM, $NaHCO_3$: 4.2 mM, $CaCl_2$: 1.3 mM, $MgCl_2$: 0.5 mM, $MgSO_4$: 0.4 Mm, HEPES: 10 mM, D-glucose: 5.6 mM) are performed in order to remove the dead cells which anarchically release radioactivity. Next, the cells are incubated with 500 μl of load (1 μCi/ml of $^{125}$INa) for 30 min for the CHO-WT cells or 1 h for the CF15 and Calu-3 cells. The iodide forms an equilibrium on either side of the cell membrane. The robot (Multi-PROBE, Packard) carries out the following steps: the load medium is rinsed with efflux medium in order to remove the extracellular radioactivity. The supernatant is collected every minute in hemolysis tubes and the medium is replaced with an equivalent volume (500 μl). No drug is added to the samples collected for the first 3 minutes, they make it possible to obtain a stable baseline, characterizing the passive outflow of the I ions. The next 7 samples are obtained in the presence of the test molecule. At the end of the experiment, the cells are lysed by adding 500 μl of NaOH (0.1N)/0.1% SDS (30 min), thus the radioactivity remaining inside the cell can be determined. The radioactivity present in the hemolysis tubes is counted in counts per minute (cpm) using a gamma counter (Cobra II, Packard). The results in cpm are expressed in the form of the rate of outflow of radioactive iodide (R) according to the following formula: $R(min^{-1})=[\ln(^{125}I\ t_1)-\ln(^{125}I\ t_2)]/(t_1-t_2)$ with $^{125}I\ t_1$: cpm at time $t_i$; $^{125}I\ t_2$: cpm at time $t_2$. This iodide flow is represented in the form of a curve. In order to quantify the outflow of iodide due to the administration of the test molecule, the following relative flow is calculated, which makes it possible to dispense with the basal flow: relative speed $(min^{-1})$=Rpic−Rbasal. Finally, these results are normalized so as to be able to compare the effect of the various drugs to each other. The results are presented in the form of a mean+/−SEM. Student's statistical test is used to compare the effect of the drugs to the controls (the values corresponding to $P<0.01$ are considered as being statistically significant).

M4. Test of Cytotoxicity

The MTT toxicity test is a calorimetric test which is based on the capacity of mitochondrial dehydrogenases to metabolize MTT (yellow tetrazolium salt) to formazan (purple). The absorbance, which is proportional to the concentration of dye converted, can then be measured by spectrophotometry. The cells are incubated on 96-well plates in the presence of the agent to be tested for 2 h. Three controls are prepared: 100% living cells: cells with no agent; 0% living cells: cells left in the open air; blank: medium with no cell. The cells are rinsed with RPMI medium with no phenol red so that the color of the medium does not interfere with the measurements of absorbance. Next, they are incubated for 4 h with 100 μl of RPMI solution supplemented with MTT (0.5 mg/ml). The medium is then removed, the addition of 100 μl of DMSO makes it possible to solubilize the converted dye (formazan). The absorbance is measured by spectrophotometry at 570 nm (purple); 630 nm (background noise). In order to get rid of the background noise, the following calculation is made: $OD_{real}=OD_{570\ nm}-OD_{630\ nm}$. Next, the results are normalized relative to the controls (100% and 0% of living cells) and are presented in the form of a mean+/−SEM.

Results

R1. Effect of Guanabenz on the Addressing of delF508 in CF15 Cells

The study of the addressing of the delF508-CFTR protein is carried out by combining pharmacology, cell imaging, biochemical test and electrophysiological approaches on human pulmonary epithelial CF15 cells homozygous for the delF508 deletion.

For each experiment, the addition of forskolin (fsk) 1 μM allows the activation of CFTR when the latter is attached to the membrane. Thus, an iodide efflux may be observed if the addressing of delF508 has been restored.

The results, which are presented in the form of a histogram, were normalized relative to a reference treatment (treatment of the cells with MPB-91 250 μM for 2 h) for which it is considered that a 100% CFTR activity is present.

The results of the activation of delF508-CFTR in CF15 cells after treatment with guanabenz are presented in FIG. 1 (the results relating to an anti-prion compound, namely 6AP (6-aminophenanthridine) are also given). The iodide efflux experiments are carried out after 2 h of incubation with 100 μm of the test compound or in the absence of this compound. The CF15 cells, treated for 24 h at 27° C., were used as positive control and the untreated CF15 cells as negative control (37° C.).

The dose-response results after 2 h of treatment with guanabenz are presented in FIG. 2A. FIG. 2B gives the pharmacological profile of CFTR channels in CF15 cells after 2 h of incubation with 100 μM of guanabenz.

The work carried out has shown that the treatment of the CF15 cells (F508del/F508del) with guanabenz allows readdressing of the mutated protein F508del-CFTR to the membrane.

The iodide efflux experiments showed that guanabenz allows readdressing of the protein F508del-CFTR after 2 h of treatment with an $EC_{50}$ of 40 μM. Furthermore, these experiments showed a competition between guanabenz and MG132, a proteasome inhibitor, and between guanabenz and swainsonine, a mannosidase inhibitor. It is evident from these results that guanabenz allows readdressing of the protein F508del-CFTR by the inhibition of the degradation pathway and/or it is possible to modulate the state of glycosylation of the protein inhibiting its interaction with the chaperones of the endoplasmic reticulum (ER).

The table which follows gives a summary of competition experiments carried out by the iodide efflux technique between guanabenz and the chaperone machinery of the ER.

| | BFA 20 μM | Tunicamycin 10 μM | Swainsonine 100 μM | Castanospermine 100 μg/l | Thapsigargin 10 μM | MG132 20 μM | Geldanamycin 2.5 μg/ml |
|---|---|---|---|---|---|---|---|
| Potentiation of the effect of guanabenz | | ** | * | *** | *** | ns | *** |
| | | Glycosylation inhibitors | | Calnexin inhibitors | | Pathway of degradation of the inhibitors | |

An inhibition of the effect of guanabenz by Brefeldine-A (BFA), an inhibitor of vesicular ERGIC traffic, is observed, which shows that guanabenz induces readdressing of delF508-CFTR.

No modulation of the effect of guanabenz is observed in the presence of MG132, a proteasome inhibitor, revealing a competition between guanabenz and MG132. A low potentiation of the effect of guanabenz is observed in the presence of swainsonine, a mannosidase inhibitor, which shows a potential action of guanabenz on the glycosylation of CFTR.

Example of Formulation

A solution for inhalation with a vial nebulizer is prepared from sodium chloride, dehydrated calcium chloride and water for injection.

Guanabenz, or a guanabenz derivative, is added as active ingredient. The solution is formulated in 2.5 ml vials. Vials containing 5, 10 or 20 mg of guanabenz or of guanabenz derivatives are thus prepared.

BIBLIOGRAPHY REFERENCES

BECQ et al. (1999) Journal of Biological Chemistry 274, 27415-27425.

DORMER et al. (2001) Journal of Cell Science 114, 4073-4081.

The invention claimed is:

1. A method of treating cystic fibrosis comprising administering to a person in need of said treatment a compound of the following formula (I):

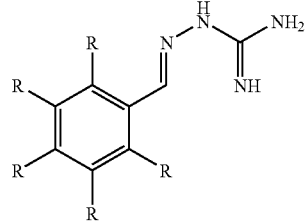

(I)

wherein R is H or Cl and the phenyl group contains at least two substituents, or a pharmaceutically acceptable salt of the compound.

2. The method of claim 1 wherein the compound is of the following formula (II):

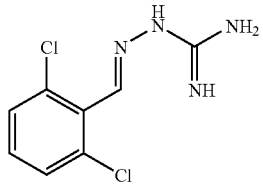

(II)

or a pharmaceutically acceptable salt thereof.

3. The method of claim 1, wherein the compound is the acetate salt of the following acetate of formula (III):

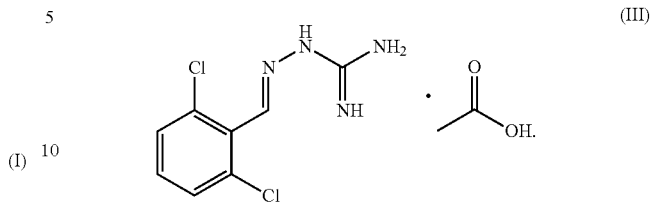

(III)

4. The method of in claim 1, wherein the molecule is of the following formula (IV):

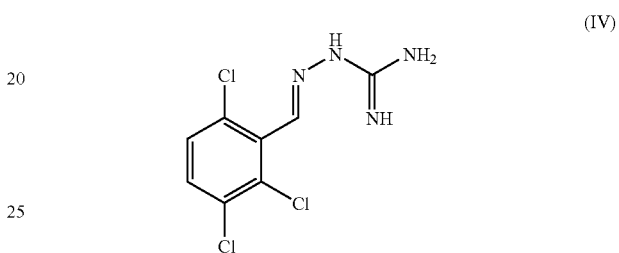

(IV)

or of a pharmaceutically acceptable salt.

5. The method of claim 1, wherein said compound is administered in the form of a tablet or capsule.

6. The method of claim 1 wherein said compound is administered by injection, in the form of a solution.

7. The method of claim 1 wherein the compound is administered in aerosol form.

8. The method of claim 1 wherein the compound is administered in the form of a gelatin capsule or sugar-coated tablet.

\* \* \* \* \*